United States Patent [19]

Schuchardt et al.

[11] Patent Number: 4,788,359

[45] Date of Patent: Nov. 29, 1988

[54] PROCESS AND APPARATUS FOR RECOVERING 1,2-DICHLOROETHANE FROM OFF-GAS

[75] Inventors: Kurt Schuchardt, Brühl; Harald Scholz, Erftstadt; Erich Niehus, Bornheim; Harald Adam, Erftstadt, all of Fed. Rep. of Germany

[73] Assignee: Hoechst Aktiengesellschaft, Fed. Rep. of Germany

[21] Appl. No.: 78,372

[22] Filed: Jul. 27, 1987

[30] Foreign Application Priority Data

Aug. 8, 1986 [DE] Fed. Rep. of Germany ....... 3626853

[51] Int. Cl.$^4$ .................. C07C 17/15; C07C 17/38
[52] U.S. Cl. .................. 570/243; 570/245; 570/212; 55/162; 422/116
[58] Field of Search .......... 570/243, 245, 262; 55/162

[56] References Cited

U.S. PATENT DOCUMENTS 3,186,144  6/1965  Dow ..................................... 55/162
3,238,701  3/1966  Holt ..................................... 55/162
4,310,713  1/1982  Legutke et al. .

FOREIGN PATENT DOCUMENTS 1483831  8/1977  United Kingdom .

Primary Examiner—Howard T. Mars
Attorney, Agent, or Firm—Connolly and Hutz

[57] ABSTRACT

1,2-dichloroethane is continuously and completely removed and recovered from the off-gas obtained during the production of 1,2-dichloroethane by subjecting ethylene to an oxychlorination reaction with hydrogen chloride and oxygen. The off-gas is initially contacted with active carbon, then incinerated at temperatures higher than 900° C. and ultimately freed from hydrogen chloride and chlorine, and the active carbon is freed from 1,2-dichloroethane and regenerated by treating it with hot steam. More particularly, the off-gas loaded with the 1,2-dichloroethane and having a temperature of 1° C. to 10° C. is heated to a temperature at least 20° C. higher than the respective dew point of water and contacted with the active carbon.

5 Claims, 1 Drawing Sheet

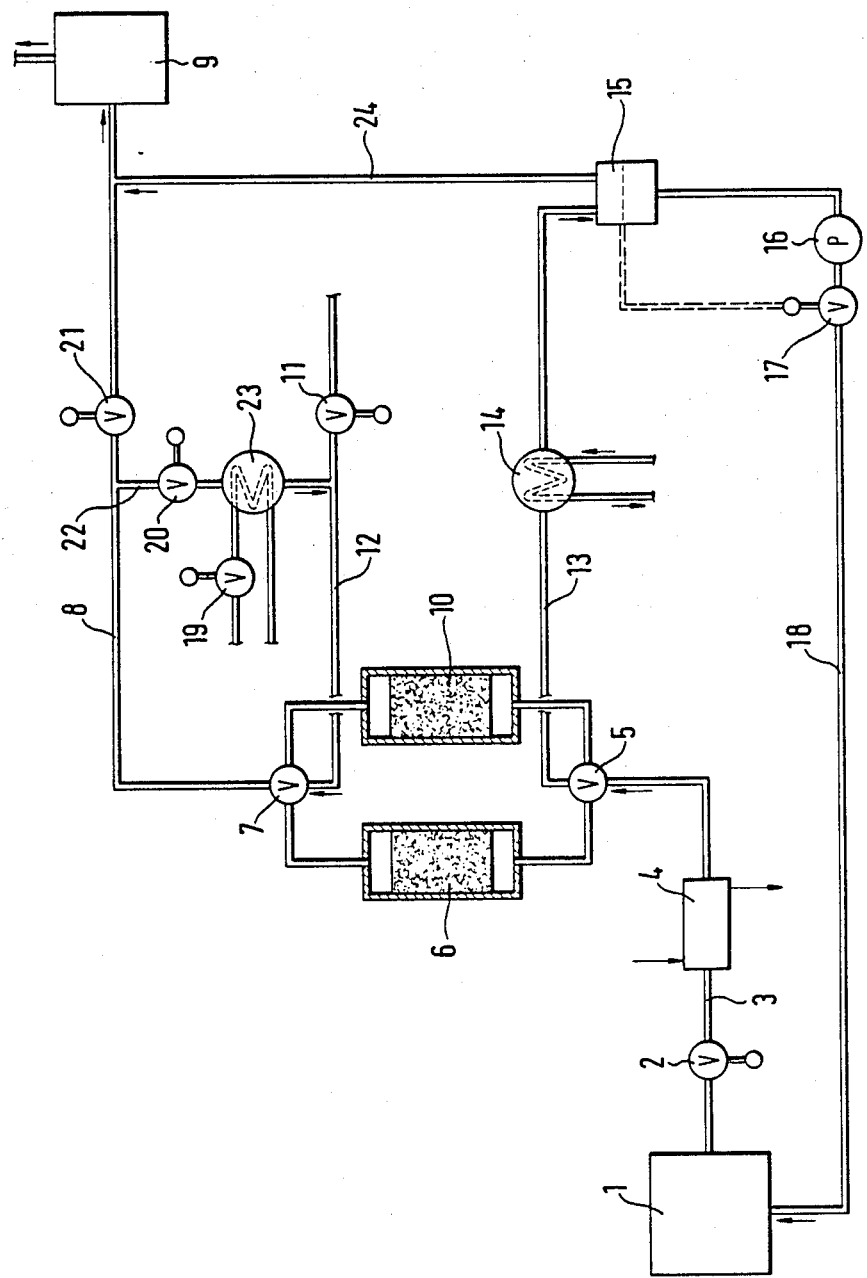

PROCESS AND APPARATUS FOR RECOVERING 1,2-DICHLOROETHANE FROM OFF-GAS

This invention relates to a process for completely removing and recovering 1,2-dichloroethane from the off-gas which is obtained during the production of 1,2-dichloroethane by subjecting ethylene to an oxychlorination reaction with hydrogen chloride and oxygen, wherein the off-gas is initially contacted with active carbon, then incinerated at temperatures higher than 900° C. and ultimately freed from hydrogen chloride and chlorine, and the active carbon is freed from 1,2-dichloroethane and regenerated by treating it with hot steam.

In industry, ethylene is oxychlorinated to give 1,2-dichloroethane. The feed materials, namely ethylene, hydrogen chloride gas and molecular oxygen are used in approximately stoichiometric proportions (1:2:0.5), preferentially however with an excess of ethylene and oxygen (1:1.9:0.6), and reacted in gas phase in contact with a Deacon-catalyst (e.g. $CuCl_2$ on an $Al_2O_3$-carrier) at elevated temperature (e.g. 200°–250° C.) and under increase pressure (e.g. 1.7–5.0 bars) to give 1,2-dichloroethane. The reaction can be effected in a fixed bed or flow bed reactor. Modern oxyclorination processes use pure oxygen instead of air to reduce the off-gas quantities and avoid the disposal thereof. Processes of this kind have been disclosed in German Specifications Nos. DE-27 18 878 C3 and 27 42 409 C3. Upon the use of pure or high grade oxygen, as little as 2 to 10% (about 16–80 $m^3/t$ 1,2-dichloroethane) of the off-gas quantities normal for the use of air (about 800 $m^3$ per ton 1,2-dichloroethane, measured under standard conditions) are obtained.

The gas coming from the reaction zone which inter alia contains 0.1–1.0 vol.% $C_2H_4$ and 4–8 vol.% $O_2$, is initially cooled to 80°–100° C. by contacting it with injected water, then indirectly to 35°–40° C. with water and ultimately to 1°–10° C. with cooling brine, in a plurality of stages. During that treatment, the reaction products, principally 1,2-dichloroethane and water, are condensed and in the end worked up.

The off-gas coming from the last condensing stage is saturated with 1,2-dichloroethane and steam, consistently with the pressure and temperature selected. It contains unreacted ethylene and molecular oxygen, depending on the excess quantity used, and also carbon oxides which are by-products obtained by combustion of ethylene, nitrogen, which is used for scavenging and measuring, and finally low-boiling organic substances in slight concentration.

The off-gas is compressed, enriched with molecular oxygen to 10–30 vol% $O_2$ and recycled to the reactor, in which the oxygen again undergoes reaction with ethylene and hydrogen chloride to give 1,2-dichloroethane. A quantity of offgas which just corresponds to the quantity of nitrogen admitted and the quantity of gaseous by-products, chiefly carbon oxides, formed is taken from that cycle via a control device installed for maintaining a constant pressure in the reactor system.

German Specification No. DE-24 00 417 C3 discloses a process for removing air-polluting off-gas obtained during the industrial synthetic production of dichloroethane by subjecting ethylene to an oxychlorination reaction, wherein the off-gas is initially condensed at temperatures between −30° and +50° C., preferentially between −10° and +10° C., and then contacted with active carbon, whereby the organic contaminants become partially adsorbed and residual combustible constituents of the off-gas are incinerated at temperatures between 500° and 2000° C.

In this process, however, the oxygen is preferentially used in the form of air as inter alia results from the gas analyses disclosed in Examples 1 and 2 of that specification (low CO and $CO_2$-concentrations due to strong dilution by atmospheric nitrogen). The immense quantities of the resulting off-gas which call for the use of appropriately dimensioned apparatus equipment and imply high energetic depense render this process commercially unattractive for regeneration and uncompetitive with those conventional methods which are based on the adsorption with an organic solvent, e.g. kerosene.

In the process disclosed in German Specification No. DE-24 00 417 C3, the off-gas presumably has the temperature with which it leaves the last condensing stage, when it is contacted with the active carbon. This is −5° C. in Example 1 of that Specification; as a result, the dichloroethane is adsorbed at a rate as low as 90%. At temperatures close to the dew point of water, the steam contained in the off-gas is adsorbed concurrently with the 1,2-dichloroethane by the active carbon and naturally affects the power of the active carbon for adsorbing organic substances, especially 1,2-dichloroethane.

In addition, cooling steam-saturated gas to a temperature lower than 0° C. leads to the formation of ice causing condensers to become clogged within short periods of time and making further operation impossible.

The present invention now unexpectedly provides a process permitting 1,2-dichloroethane to be recovered substantially completely from the off-gas originating from an oxychlorination reaction which is carried out with the use of substantially pure oxygen, which comprises heating the off-gas loaded with the 1,2-dichloroethane and having a temperature of 1° C.–10° C. to a temperature at least 20° C. higher than the respective dew point of water, and contacting it with active carbon.

Further preferred and optional features of the process of this invention provide:

(a) for the off-gas loaded with the 1,2-dichloroethane to be heated to 25° C.–35° C.;

(b) for the active carbon used to be one having an active BET-surface area of at least 1200 $m^2/g$;

(c) for the active carbon to be placed in two zones resembling one another in one of which the 1,2-dichloroethane is being adsorbed from the off-gas over a period of 8 to 18 hours whereas the other zone is being regenerated in three stages;

(d) for the off-gas to remain over a period of at least 10 seconds, preferably 20–60 seconds, in the active carbon-zone adsorbing the 1,2-dichloroethane;

(e) for the active carbon-zone loaded with the 1,2-dichloroethane to be charged in the first regenerating stage with steam under a pressure of 4 to 10 bars and freed from the 1,2-dichloroethane, for it to be dried in the second regenerating stage by means of off-gas heated to 100°–150° C. and being free from 1,2-dichloroethane, and for it to be cooled in the third regenerating stage by injecting off-gas from 1,2-dichloroethane, for condensed 1,2-dichloroethane and condensed steam to be recycled into the oxychlorination reaction and for the offgas to be incinerated;

(f) for the switching over from one regenerating stage to the next and from one active-carbon-zone to the other to be controlled automatically by a timed program.

The invention also relates to apparatus for continuously carrying out the process of this invention comprising: two substantially similar cylindrical adsorbers 5 which are packed with active carbon, arranged in upright position, connected together at their lower and upper ends by two junction lines, and present a height-/diameter-ratio of 5:1 to 10:1, the quantity of active carbon packed into one of the two adsorbers having an adsorbing capacity sufficient in respect of time for regenerating an identical quantity of active carbon in the respective other adsorber; a lower and upper four-way valve each in the two junction lines; a first inlet conduit for admitting 1,2-dichloroethane-containing off-gas coming from the oxychlorination facility to the lower four-way valve; a heating means in the first inlet conduit; a first outlet conduit for delivering off-gas free from 1,2-dichloroethane from the upper four-way valve to an incinerator; a second inlet conduit with a cutoff valve running to the upper four-way valve for supplying the hot steam necessary for alternately desorbing the active carbon and for supplying off-gas free from 1,2-dichloroethane for drying or cooling the desorbed active carbon; a third junction line with heat exchanger conveying off-gas free from 1,2-dichloroethane between the first outlet conduit and second inlet conduit; a second outlet conduit for delivering hot steam containing 1,2-dichloroethane and steam-saturated off-gas and condensing agent from the lower four-way valve to a separator for separation and simultaneous phase separation of condensed 1,2-dichloroethane and water.

Further preferred and optional features of the invention provide:

(g) for the apparatus to comprise a third outlet conduit for conveying off-gas free from 1,2-dichloroethane from the separator to the incinerator;

(h) for the apparatus to comprise a fourth outlet conduit for delivering 1,2-dichloroethane and condensed matter from the separator fitted with a level control to the oxychlorination facility.

The three-stage regeneration of active carbon in accordance with this invention differs basically from the process disclosed in German Specification No. DE-24 00 417 C3 in which the active carbon is regenerated once with steam of about 100° C. (about 1 bar). In clear contrast with this, the process of this invention comprises regenerating the active carbon in the first stage with considerably hotter steam, namely under 4 to 10 bars, drying it in the second stage with hot off-gas free from 1,2-dichloroethane and cold-blowing it in the third stage with cold off-gas free from 1,2-dichloroethane. The 1,2-dichloroethane recovered is continuously taken from the separator so that the off-gas free from 1,2-dichloroethane used in the drying and cold-blowing stage is prevented from again resorbing 1,2-dichloroethane in the separators of the second and third stages.

BRIEF DESCRIPTION OF THE DRAWING

The process and apparatus of this invention will now be described with reference to the accompanying flow scheme:

With reference to the drawing thereto:

Off-gas taken from an oxychlorination facility 1 through pressure-retaining valve 2 is heated in line 3 by means of heater 4 to a temperature at least 20° C. higher than the dew point of water and transported through four-way valve 5 to adsorber 6 in which it is freed from 1,2-dichloroethane by adsorbing it on active carbon. The gas so treated then flows through four-way valve 7 and line 8 to an incinerator 9 unless it is needed for regenerating adsorber 10 and therefore passed through said adsorber 10, prior to delivering it to the incinerator. Immediately after the automatic switch over to adsorber 6, one commences regenerating the active carbon in adsorber 10 by opening steam valve 11. Steam under a pressure of 4–10 bars travels through line 12 and four-way valve 7 from above to below through the adsorber 10, expelling the 1,2-dichloroethane from the active carbon. 1,2-dichloroethane and steam flow through four-way valve 5 and line 13 to condenser 14 in which the two materials are condensed out and run into separator 15. In separator 15, the phases are separated from one another, the 1,2-dichloroethane forming the lower and $H_2O$ the upper phase, due to different density. In this way, pump 16 and level control 17 commence at once recycling 1,2-dichloroethane, however together with a portion of water, through line 18 into the oxychlorination facility 1. Just a fraction of water always remains as the stable phase in separator 15.

After a predetermined period of time, the first regenerating stage is automatically terminated and the second regenerating stage, i.e. the step of drying the active carbon, is initiated as follows: steam regulating valve 11 is closed; steam regulating valve 19 is opened; regulating valve 20 is opened; regulating valve 21 is closed.

The direction of flow of the off-gas freed from 1,2-dichloroethane in adsorber 6 is thereby altered and the gas assuming a temperature of 100°–150° C. while travelling through line 22, valve 20, heat exchanger 23, line 12 and four-way valve 7, now flows through adsorber 10 and from there through four-way valve 5, line 13, condenser 14, separator 15, line 24 and line 8 to incinerator 9. Steam regulating valve 19 is closed after the programmed time and the active carbon in adsorber 10 is cooled the same way as just described in the third regenerating stage, prior to the programmed switching ove of the two four-way valves 5 and 7 to the other adsorber re-initiating the whole operation.

EXAMPLE 1

$C_2H_4$, HCl and $O_2$ in a ratio of about 1:1.9:0.6 were introduced into a flow bed reactor packed with a Deacon catalyst (e.g. $CuCl_2/Al_2O_3$) and reacted at 220° C. under 4 bars. The materials underwent oxychlorination chiefly to 1,2-dichloroethane and water. $C_2H_4$ were used in excess in order to make it possible for the HCl to react as completely as possible and to avoid corrosion of the apparatus.

The reaction gas coming from the reactor was cooled to 90° C. in a first condensing stage by injecting water, alkalized if desired. Next, the reaction gas was cooled in two condensing stages, initially with water to 38° C. and then with brine to 7° C., whereby 1,2-dichloroethane and water became condensed out.

The gas coming from the third condensing stage with a temperature of 7° C. contains $N_2$; small quantites of it were introduced together with the feed gases into the reactor for scavenging and measuring; the gas which became gradually more concentrated also contained CO and $CO_2$, which are reaction by-products that are obtained by the combustion of $C_2H_4$ and equally become gradually enriched until establishment of an equilibrium between newly forming and removed material. The gas also contained 0.37 vol.% $C_2H_4$ and 5.9 vol.% $O_2$, corresponding to the excess used, and less than 1 vol.% low-boiling organic by-products. In addition, it was saturated with 1,2-dichloroethane and water consistently with the pressure and temperature selected.

The reaction gas had the folllwing quantitative composition in vol.%, the water content being ignored:

|  | upstream adsorber | downstream adsorber |
| --- | --- | --- |
| $H_2$ | 0.21 | 0.23 |
| Ar | 2.8 | 2.8 |
| $O_2$ | 5.9 | 6.1 |
| $N_2$ | 53.9 | 53.9 |
| $CH_4$ | 0.036 | 0.037 |
| CO | 2.9 | 2.9 |
| $CO_2$ | 32.5 | 33.3 |
| $C_2H_4$ | 0.37 | 0.42 |
| $C_2H_6$ | 0.23 | 0.24 |
| $CH_3Cl + CH_2 = CHCl$ | 0.38 | 0.02 |
| $C_2H_5Cl + CH_3CHO$ | <0.02 | <0.02 |
| 1,2-dichloroethane | 1.0 | <1 ppm |

It was compressed to approximately 6 bars, enriched with $O_2$ to 20 vol.% $O_2$ and recycled into the oxychlorination reactor in which the $O_2$ again underwent reaction.

Prior to compressing the gas, a quantity of off-gas which accurately corresponded to the plus of inert gas and gaseous by-products was removed through a pressure regulating control maintaining the pressure in the reactor and gas cycle constant. In the present Example, this was a quantity of 900 $m^3$/h off-gas, corresponding to 70 $m^3$ off-gas per ton 1,2-dichloroethane, under standard conditions (0° C., 1.013 bar).

Along a heating path, the off gas of 7° C. and 1.7 bar was heated to 30° C., i.e. to a temperature 23° C. above the dew point of water whereby the adsorption capacity of the active carbon for 1,2-dichloroethane was optimized. Next, the off-gas was passed through one of the two cylindrical adsorbers (height: 7.0 m; diameter: 0.9 m; volume 4.45 $m^3$; height/diameter-ratio=7.7:1) packed with active carbon having a BET-surface of 1400 $m^2$/g, and the gas was in this way freed substantially completely from the 1,2-dichloroethane to less than 1 ppm. Gas analysis indicated that the active carbon also adsorbed methyl chloride and vinyl chloride; they could be desorbed with steam, but their recovery was not of interest.

Next, the off-gas was introduced direct into an incinerator, or where it was required to be used for regenerating, it was introduced into the second adsorber for further treatment. The residual organic constituents were incinerated at a temperature of more than 900° C., and HCl and chlorine were removed in a downstream scrubbing stage, and the off-gas was ultimately allowed to escape into the atmosphere.

The adsorbers were two containers similar to one another which had a volume sufficient for the adsorber to adsorb 1,2-dichloroethane over the period of time needed for regenerating the other.

The switching over from the adsorbing to the regenerating adsorber occurred automatically as programmed in 12 hours intervals by means of two four-way valves. In other words, one of the two adsorbers was in operation, when the other was regenerated in three stages.

The first stage comprises: desorbing the 1,2-dichloroethane with steam of 8 bars. 1,2-dichloroethane and steam were condensed out and ran into a separator in which they separated due to their insolubility and different density. The specifically denser 1,2-dichloroethane formed the lower phase and was directly repumped to the oxychlorination facility, owing to the level control provided in the separator; a portion of the upper phase, which was water, followed.

The second stage comprises: drying the active carbon with 900 $m^3$/h (S.T.P.) off-gas previously freed from 1,2-dichloroethane and heated to 124° C.; the off-gas travelled through the adsorber, condenser and separator to the incinerator.

The third stage comprises: cold-blowing with the unheated off-gas (900 $m^3$/h, S.T.P. 30° C.) of the second stage.

All operations necessary for regenerating and switching from one adsorber to the other occurred automatically as programmed.

EXAMPLE 2 (comparative Example)

The procedure was as in Example 1, but only 860 $m^3$/h off-gas, corresponding to 68 $m^3$ off-gas per ton 1,2-dichloroethane, determined under standard conditions, was taken from the gas cycle of the oxychlorination facility. The off-gas removed at 7° C. was not heated so that the adsorption in contact with active carbon took place at 7° C. The following gas analysis (vol.%) indicated that the 1,2-dichloroethane content was as high as 0,13 vol.%.

|  | upstream reactor | downstream reactor |
| --- | --- | --- |
| $H_2$ | 0.24 | 0.24 |
| Ar | 2.90 | 2.90 |
| $O_2$ | 6.00 | 6.00 |
| $N_2$ | 55.00 | 55.10 |
| $CH_4$ | 0.04 | 0.04 |
| CO | 3.0 | 3.0 |
| $CO_2$ | 33.2 | 33.4 |
| $C_2H_4$ | 0.51 | 0.50 |
| $C_2H_6$ | 0.21 | 0.21 |
| $CH_3Cl + CH_2 = CHCl$ | 0.31 | 0.04 |
| $C_2H_5Cl + CH_3CHO$ | < 0.02 | < 0.02 |
| 1,2-dichloroethane | 1.0 | 0.13 |

We claim:

1. A continuous process for completely removing and recovering 1,2-dichloroethane from the off-gas obtained during the production of 1,2-dichloroethane by subjecting ethylene to an oxychlorination reaction with hydrogen chloride and oxygen, the off-gas being initially contacted with active carbon, then incinerated at temperatures higher than 900° C. and ultimately freed from hydrogen chloride and chlorine, and the active carbon being freed from 1,2-dichloroethane and regenerated by treating it with hot steam, which comprises: heating the off-gas loaded with the 1,2-dichloroethane and having a temperature of 1° C. to 10° C. to a temperature at least 20° C. higher than the respective dew point of water and contacting it with the active carbon, the active carbon being placed in two zones resembling one another and in one of which the 1,2-dichloroethane is being absorbed from the off-gas over a period of 8 to 16 hours, the other zone being regenerated in three stages, charging the active carbon zone loaded with the 1,2-dichloroethane in a first regenerating stage with steam under a pressure of 4 to 10 bars and freeing it from the 1,2-dichloroethane, drying it in a second regenerating stage by means of off-gas heated to 100°–150° C. and being free from 1,2-dichloroethane, and cooling it in a third regenerating stage by injecting off-gas free from 1,2-dichloroethane, condensing the freed 1,2-dichloroethane and steam, the condensed 1,2-dichloroethane and a portion of the condensed steam being recycled into the oxychlorination reaction and the off-gas being incinerated.

2. A process as claimed in claim 1, wherein the off-gas loaded with the 1,2-dichloroethane is heated to 25° C. to 35° C.

3. A process as claimed in claim 1, wherein the active carbon used is one having an active BET-surface area of at least 1200 m$^2$/g.

4. A process as claimed in claim 1, wherein the off-gas is allowed to remain over a period of at least 10 seconds in the active carbon zone adsorbing the 1,2-dichloroethane.

5. A process as claimed in claim 1, wherein the switching over from one regenerating stage to the next and from one active-carbon zone to the other is controlled automatically by a timed program.

* * * * *